United States Patent
Garlick

(12) 
(10) Patent No.: US 6,537,494 B2
(45) Date of Patent: Mar. 25, 2003

(54) SUPER-CHARGED OZONEATED FOG FOR SURFACE STERILIZATION

(75) Inventor: Todd Garlick, Pasco, WA (US)

(73) Assignee: Holographic Engineering LLC, Richland, WA (US)

( * ) Notice: Subject to any disclaimer, the term of this patent is extended or adjusted under 35 U.S.C. 154(b) by 0 days.

(21) Appl. No.: 10/135,896

(22) Filed: Apr. 29, 2002

(65) Prior Publication Data

US 2002/0192110 A1 Dec. 19, 2002

Related U.S. Application Data

(62) Division of application No. 09/498,213, filed on Feb. 4, 2000, now Pat. No. 6,379,633.

(51) Int. Cl.[7] .................................................. A61L 9/00
(52) U.S. Cl. .............................. 422/27; 239/4; 422/28; 422/32; 422/186.07; 422/305; 422/306; 426/326; 426/332
(58) Field of Search ................................ 422/305, 306, 422/186.07, 27, 28, 32; 239/4; 426/326, 332

(56) References Cited

U.S. PATENT DOCUMENTS

| | | | | |
|---|---|---|---|---|
| 4,106,459 A | * | 8/1978 | Asai et al. ................... | 123/439 |
| 5,387,403 A | * | 2/1995 | Ikeuchi et al. .............. | 422/292 |
| 5,882,591 A | * | 3/1999 | Kekez .......................... | 422/28 |
| 5,938,117 A | * | 8/1999 | Ivri ............................... | 239/4 |
| 6,029,911 A | * | 2/2000 | Watanabe et al. ........... | 239/427 |
| 6,379,633 B1 | * | 4/2002 | Garlick ........................ | 422/305 |

* cited by examiner

Primary Examiner—Krisanne Thornton
(74) Attorney, Agent, or Firm—Barry L. Davison; Davis Wright Tremaine LLP

(57) ABSTRACT

There is disclosed a sterilizing fog, characterized by droplet size range, vapor density range, sterilant concentration range and sterilant concentration within the droplets. Specifically, there is disclosed a fog achieved by an apparatus combining pressure, temperature and acoustics to form a super-charged ozoneated water and an apparatus that creates small micro droplets which form a highly concentrated sterilizing fog. Specific sterilants used are ozone, chlorine and chlorous acid generating compositions such as sodium hypochlorite, or combinations thereof.

5 Claims, 4 Drawing Sheets

SUPER-CHARGED OZONEATED FOG FOR SURFACE STERILIZATION

This application is a division of Ser. No. 09/498,213 filed Feb. 4, 2000 now U.S. Pat. No. 6,379,633.

TECHNICAL FIELD OF THE INVENTION

The present invention provides a sterilizing fog, characterized by droplet size range, vapor density range, sterilant concentration range and sterilant concentration within the droplets. Specifically, the inventive fog is achieved by an apparatus combining pressure, temperature and acoustics to form a super-charged ozoneated water and an apparatus that creates small micro droplets which form a highly concentrated sterilizing fog. Specific sterilants used are ozone, chlorine and chlorous acid generating compositions such as sodium hypochlorite.

BACKGROUND OF THE INVENTION

Food processing and food safety has increasingly relied upon techniques to remove or eliminate harmful microbial organisms from the surfaces of food products. Harmful bacterial products have been found on meat food products, such as salmonella on poultry and *E. coli* H057 on various red meats. Various techniques have been developed to test for the presence of such harmful organisms but such tests, inherently, can only sample random surfaces and rely on probabilities to determine of all of the surface area of food products has either been free of such harmful organisms or effectively decontaminated.

There are many broad-spectrum sterilizing agents that are strong oxidants, such as chlorine, hypochlorite (bleach), hydrogen peroxide, and ozone or $O_3$. Although chlorine is the most common sterilizing agent in the world, ozone is commonly used to sterilize hot tubs and other public swimming pools. In addition, poultry and other meat-processing that historically has relied solely on chlorine, now frequently baths chickens in water containing ozone. However, in order for the ozone, or chlorine or any other sterilant in water to be effective, the sterilizing agent is present in a sufficient concentration within water and in contact with the organisms (and the chicken) for a sufficient period of time (inversely related to concentration) to allow the oxidizing agent to contact and kill microorganisms. It is difficult to achieve such high concentrations in an aqueous liquid. In a gaseous form most sterilizing agents are rather hazardous and difficult to control exposure time. Ozone decays in a gaseous form far too quickly to be useful for food processing. Thus, water is the preferred media for transporting ozone, chlorine, and hypochlorite to a contaminated site for oxidative anti-microbial activity.

Unfortunately, the realities of food processing are such that many food products cannot be immersed in a liquid bath (e.g., most fresh meat products and even some dry products like grains) although some moisture is allowed contact. In those instances where water immersion is not permitted, spray systems have been developed to spray a water-laden with oxidizing agent. However, spray systems do not provide a uniform coverage of the product and can utilize large amounts of water. Accordingly, spray systems employing larger droplets of water containing ozone, chlorine or hypochlorite have not been effective because of a droplet size that is too large to effect food surface penetration of irregularities. Moreover, the lower concentrations of sterilizing agents achievable in such spray systems, coupled with short exposure times, do not provide for effective oxidizing potentials and anti-microbial activity to be sufficiently effective as a decontaminating process. This is especially true of chlorine and hypochlorite that require long exposure times.

A further issue is that liquid sterilization systems or spray systems with large droplets are unable to penetrate micro-cavities on irregular surfaces of food products, such as meats (e.g., poultry or bovine). Water surface tension prevents the large drops and liquid baths from penetrating these regions and the bacteria present in micro-cavities remains undisturbed (FIG. 1 left panel).

Therefore, there is a need in the art to be able to better utilize the anti-microbial power of ozone, chlorine, hypochlorite, and other sterilizing agents, particularly within the context of food processing of meat products having irregular surfaces to hide bacteria from exposure to oxidizing agents. The present invention was made to solve this need.

SUMMARY OF THE INVENTION

The present invention provides an sterilizing agent-laden fog useful for disinfecting irregular surfaces wherein the fog comprises water and a sterilizing agent selected from the group consisting of ozone, hypochlorite, chlorine and combinations thereof, wherein the fog is characterized by droplets having an average diameter of from about 0.0005 mm to about 0.05 mm, a weight of fog concentration in a treatment space is of from about 0.08 $g/m^3$ to about 0.8 $g/m^3$. Preferably, the concentration of ozone in water of from about 0.5 ppm to about 30 ppm, the concentration of chlorine in water of from about 10 ppm to about 100 ppm, and the concentration of sodium chlorite of 0.001% to about 0.65% by weight based upon the total weight of said composition of sodium chlorite, whereby the chlorite ion concentration in the form of chlorous acid is not more than about 15% by weight of the total amount of chlorite ion concentration. Preferably, sterilizing agent is an aqueous solution consisting essentially of from about 1% to about 6% by weight of citric acid, and from about 0.001% to about 0.65% by weight based upon the total weight of said composition of sodium chlorite, such that the chlorite ion concentration in the form of chlorous acid is not more than about 15% by weight of the total amount of chlorite ion concentration.

The present invention further provides a sterilizing fog generator device for generating a sterilant fog having droplets of an average diameter from about 0.0005 mm to about 0.05 mm, comprising:

(a) an ozone gas injector for injecting gas into water and having a venturi nozzle; and (b) a vapor cell communicating with the ozone gas injector nozzle, wherein the vapor cell has a bottom and side walls and comprises an ultrasonic focused transducer located on the bottom of the vapor cell and wired to an electronic amplifier and an orifice direct toward a target for the ozone fog. Preferably, the sterilant fog is an ozone fog wherein ozone concentrations of from about 0.5% to about 20% by weight. Preferably, the ultrasonic transducer is operated at multiple frequencies of from about 0.75 MHz to about 2.0 MHz and at multiple pulse shapes, whereby the frequency and pulsed irregular wave forms control droplet size of the fog produced. Preferably, the orifice has a diameter of from about 0.1 cm to about 8 cm whereby the orifice size determines the density of the ozone fog generated. Preferably, the present invention further comprises a plurality of the vapor cells, connected in series or in parallel, and communicating to the target for the ozone fog through a single orifice.

The present invention further provides a food disinfection immersion apparatus comprising (a) a means for forming an ozone gas;

(b) a means for injecting the ozone gas into a water stream in an injection chamber, wherein the injection chamber further comprises a temperature controller, a pressure controller and an ultrasonic transducer to achieve the highest saturation level of gas in liquid; and (c) an immersion tank for disinfecting the food comprising an entry port for feeding the highly concentrated ozone water, a means for suspending the food product, and one or a plurality of ultrasonic scrubbers that agitate the food product surface microcavities to allow for deeper penetration of the highly concentrated ozone water. Preferably, the food disinfection immersion apparatus further comprises a means for injecting sodium hypochlorite and chlorine solutions into a water stream.

The present invention further provides a method for disinfecting irregular surfaces, comprising contacting a product having an irregular surface for disinfecting with a sterilizing fog, wherein the ozone fog comprises water and a sterilizing agent and wherein the fog is characterized by droplets having an average diameter of from about 0.0005 mm to about 0.05 mm, a weight of fog concentration in a treatment space of from about 0.08 g/m$^3$ to about 0.8 g/m$^3$, and an ozone concentration in water of from about 0.5 ppm to about 30 ppm. Preferably, the product having an irregular surface is a food product. Most preferably, the food product is red meat or poultry.

BRIEF DESCRIPTION OF THE DRAWINGS

FIG. 1 shows a schematic of an irregular surface of a food product (such as meat or poultry) having a micro-cavity that is often a site harboring bacterial growth (which forms the micro-cavity). The left panel shows a typical spray droplet in approximate relational scale having too much surface tension in order to penetrate and access the micro-cavity irrespective of the concentration or potency of anti-microbial oxidizing agent. The right panel shows the advantage of the inventive fog having a much smaller droplet size and an ability to access the reaches of a micro-cavity.

DETAILED DESCRIPTION OF THE INVENTION

Figures 1A, 1B:
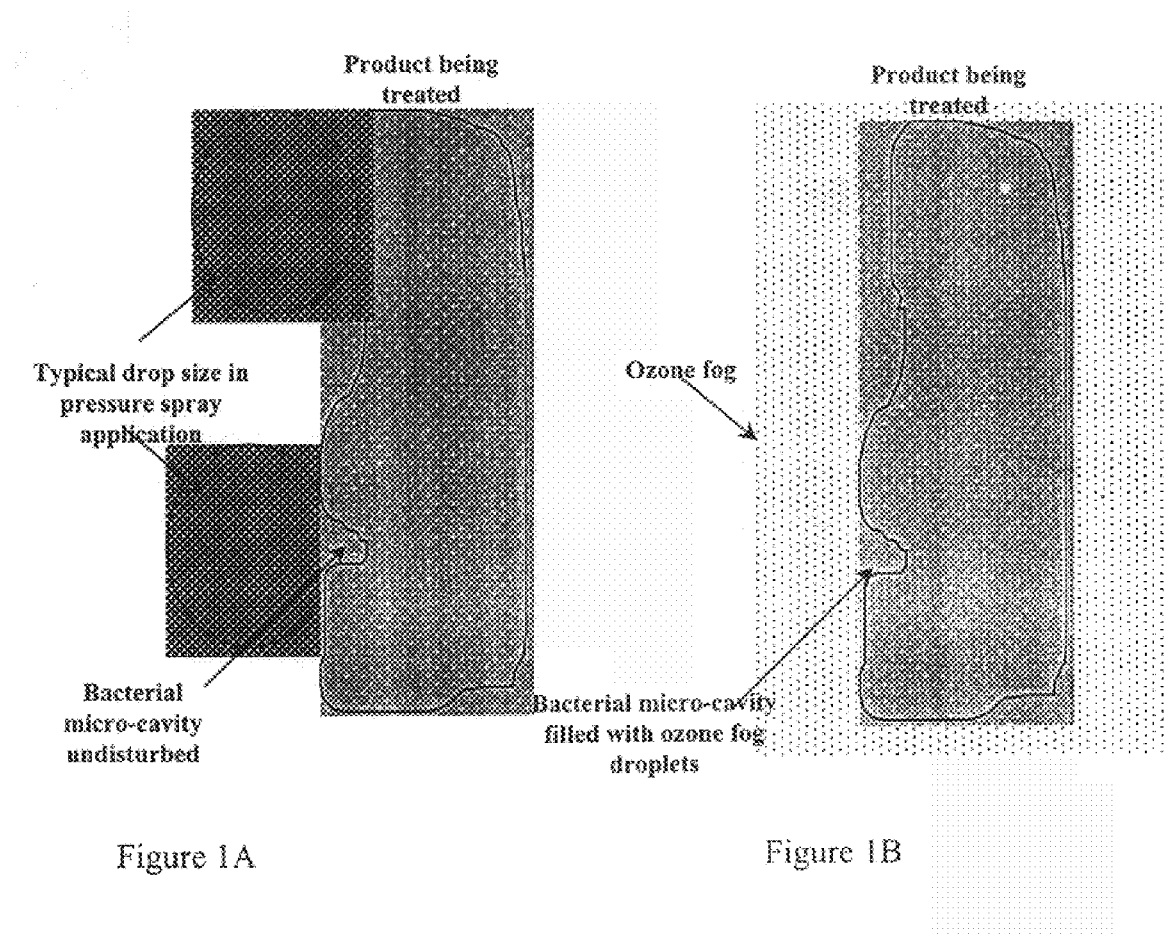

The present invention provides a more useful ozone fog that is able to access irregular surfaces of food products, such as meats (muscle tissue), due to its very small droplet size coupled with a high ozone concentration in water. The irregular surfaces of meat products can harbor microbial contamination and provide a difficult surface for penetration or access of a liquid-based anti-microbial agent. For example, rain drops and low-pressure sprayers have or provide droplet sizes ranging from 0.15 mm to 0.5 mm. The smaller droplets of the inventive fog are better able to penetrate surface irregularities with "micro-cavity" regions where contaminating microbial growth is present (FIG. 1 right panel).

Figure 4:
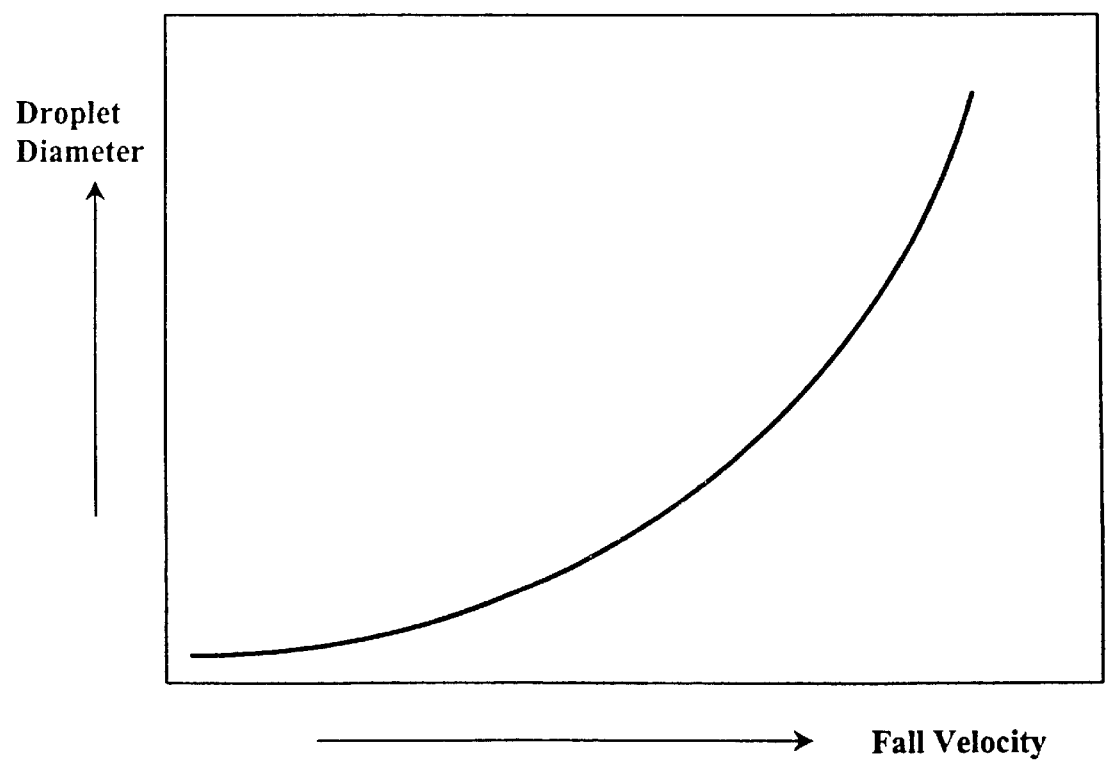
FIG. 4 shows a standard curve of fall velocity of droplet is proportional to the square of the droplet diameter.

An additional advantage of the smaller droplet size of the inventive fog is a significantly lower "fall velocity" or how fast the droplet will fall to a ground surface (see FIG. 4). The fall velocity of the droplets of the inventive fog is about 1000 times that of rain droplets or nearly 1000 cm/sec for rain compared with less than 1 cm/sec for the inventive fog (Schemenauer and Cereceda, *Water Int.*, 1994). The slower fall rate allows the inventive fog a longer contact time with the surface as it can "hover" over and adjacent to such a surface. In addition, the inventive ozone fog, having the smaller droplets, is more easily moved by fans and enclosures to fill the micro-cavities of an irregular surface and more uniformly surround surfaces for food treatment and a more even coverage.

The inventive sterilizing fog generator preferably utilizes highly ozoneated water that can be created by injecting ozone gas into a water stream, such as with a venturi nozzle 17. Additionally the ozone concentration can be increased by dissolving more ozone or another sterilant gas in the water through the use of ultrasonic transducers (14). High frequency high power sound waves cause the undissolved gas bubbles to rupture. Each time a bubble divides more gas is dissolved in the water. The ultrasonic transducer is connected to an electronic amplifier (e.g., acoustic driver 19) that is operated at multiple frequencies ranging from about 0.1 MHz to about 1 MHz.

The highly ozoneated water is used to either feed an immersion tank for direct contact with food product surfaces, or to create the inventive fog in a vapor cell (13). In the case of an ozone fog, a vapor cell is filled with ozoneated water to a defined level, wherein the vapor cell further comprises an ultrasonic focused transducer (14) mounted at the bottom of the vapor cell (that is, completely immersed with ozoneated water). The transducer is connected to an electronic amplifier (19) that can be operated at multiple frequencies. Frequencies control droplet size and thus the control of the frequency settings control the resulting droplet size. However, a frequency setting between 0.75 MHz and 1.5 MHz will produce the desired droplet size with an average diameter of between 0.0005 mm and 0.05 mm.

The vapor cell further comprises an orifice (22) to allow release of the inventive ozone fog. The density of the fog cloud released is a function of orifice size (diameter) wherein an orifice size of from about 0.1 cm to about 8 cm will produce an ozone fog having a density of between about 0.08 g/m$^3$ to about 0.8 g/m$^3$. The orifice opens up to a contact chamber where the product to be disinfected is located. There may be one or a plurality of ozone fog generating devices to communicate with the contact chamber (12). In addition, a series of fans (24) can control the flow of the inventive ozone fog and direct it to a specific target surface or object. Moreover, the contact chamber can contain an exit port to allow for recycling of the ozoneated fog back into the vapor chamber for recharging of ozone concentrations.

Figure 2:
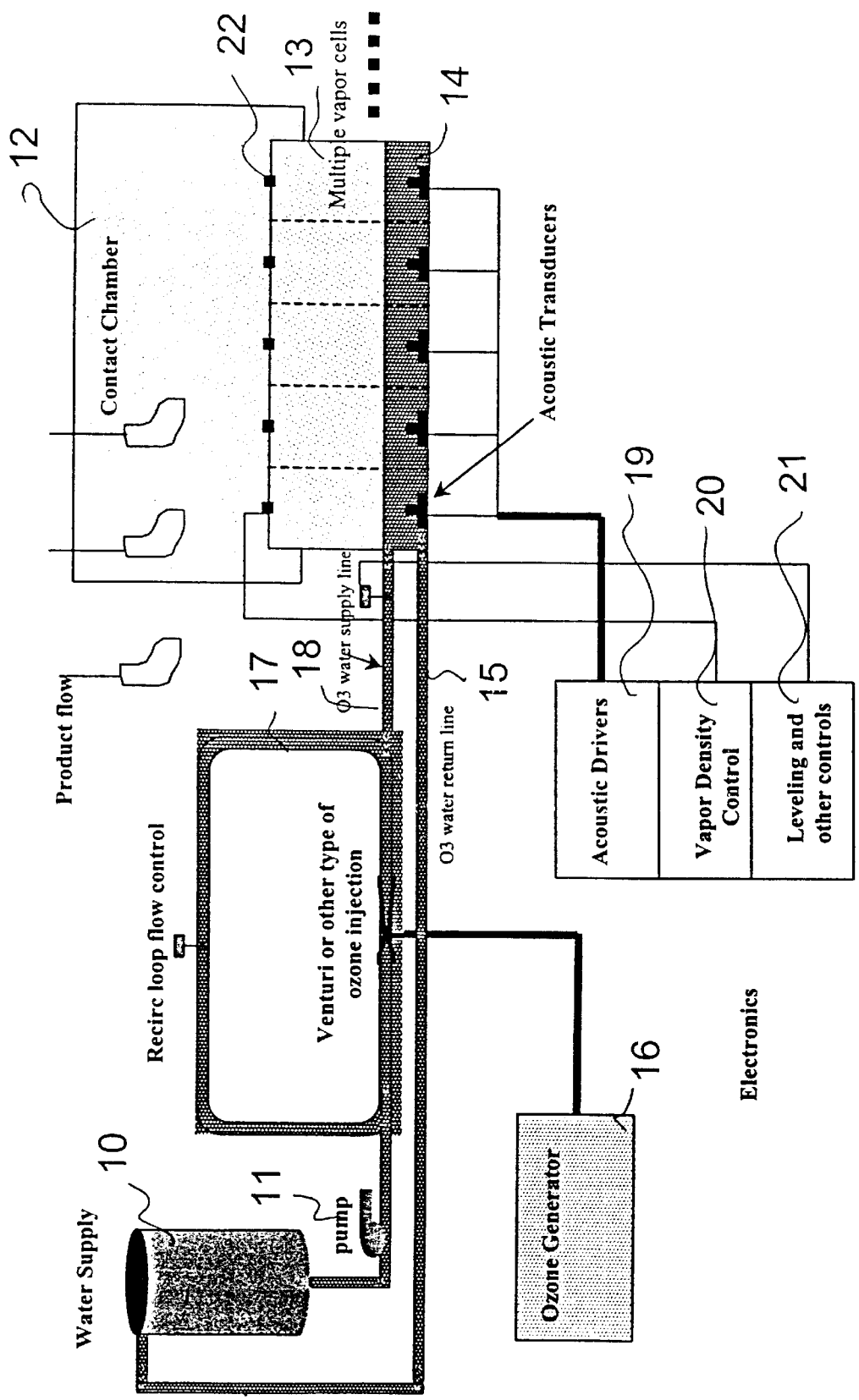
FIG. 2 shows a schematic drawing of an inventive ozone fog generating apparatus having a contact chamber with the high concentration sterilant fog for disinfecting various meat products in an assembly line fashion.
Figure 3:
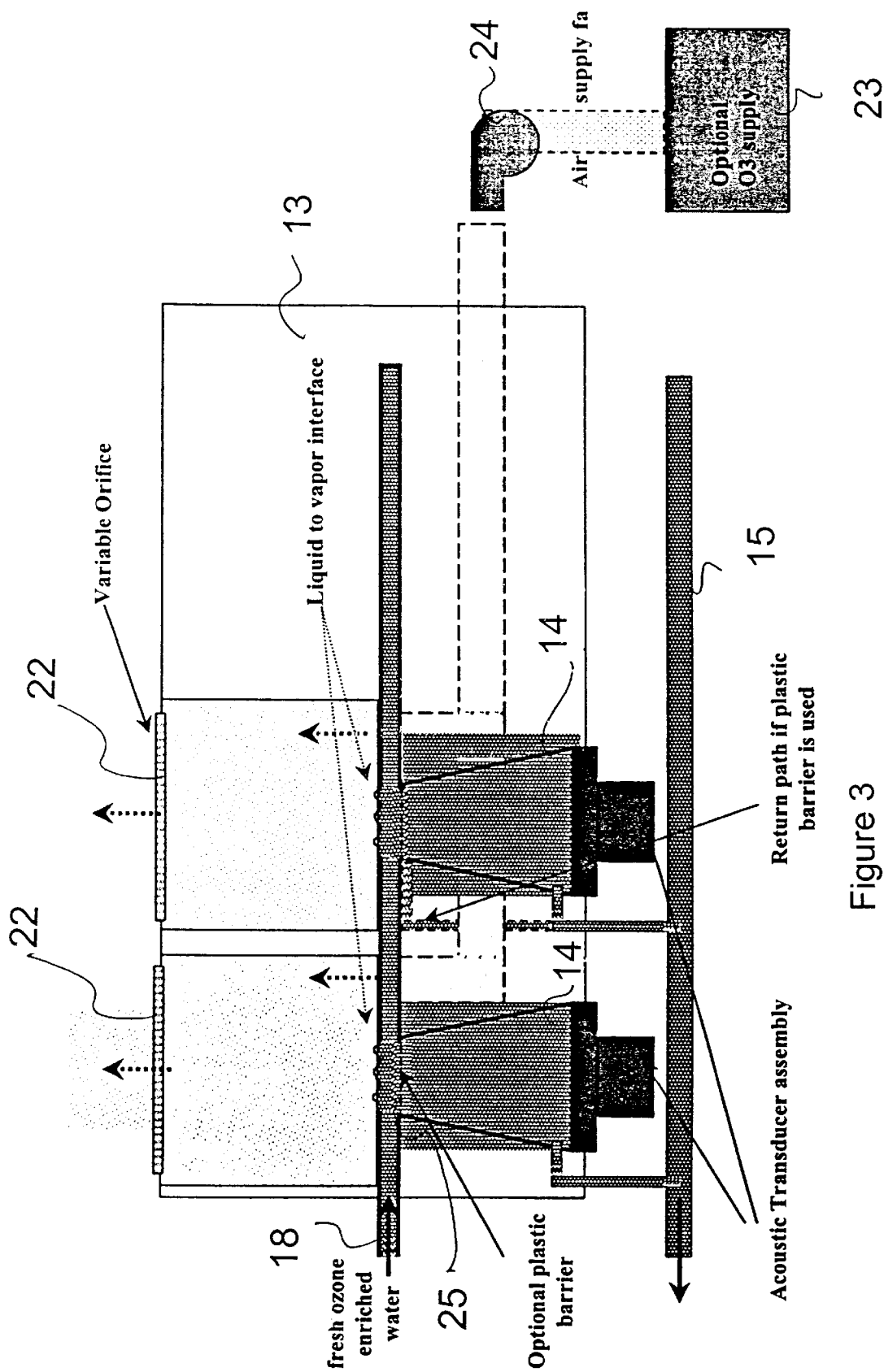
FIG. 3 shows the vapor cell component of the inventive apparatus in more detail. Specifically, acoustic transducers generate a high ozone concentrated fog in multiple vapor cells that is released through a variable orifice.

With regard to FIG. 1, A schematic diagram is provided that shows the importance of smaller droplet size able to penetrate irregular surfaces of food particles. The smaller droplet size is able to access bacterial-laden micro-cavities. With regard to FIG. 2, shows a preferred system for generating inventive ozone fog for contacting food in a food contact chamber (12). There is a water supply 10 pumped 11 to an ozone generator 16 to a recirculation loop 17 having an ozone injector such as a Venturi nozzle. The ozone is supplied to a plurality of acoustic transducers 14 via a ozone supply line 18 and returning via a return line 15. The acoustic transducers communicate with multiple vapor cells 13 and are controlled by acoustic drivers 19 that have vapor density control 20 and leveling and other controls 21. Through an orifice 22 in each vapor cell 12, the inventive ozone fog is released into contact chamber(s) 12 to sterilize food surfaces.

With regard to FIG. 3, two acoustic transducers are shown connected to a supply of fresh ozone-enriched water. The fog is formed in adjoining vapor cells. The transducers are commercial ultrasonic focused transducers, such as from Panasonic or others. Although not shown, there is a water recirculation loop to provide only the freshest ozonated water to the transducers. There is a liquid coupling cell to couple the sound to the surface as there is a distance (focal length) needed where the ultrasonic energy is focused onto the surface of the ozoneated water stream. The disruption on the surface of the water stream is from the focused ultrasonic energy to form small droplet ozone fog in the vapor cell. An air supply fan conveys the fog out of the vapor cell, through a variable orifice into a chamber. Preferably, an ozonated air supply is blown (via a fan) to clear the fog our of the vapor cells and through the variable orifice.

Alternatively, a food product may be immersed in an immersion tank (not depicted) containing highly ozoneated water. The immersion tank further comprises an entry port for feeding the highly concentrated ozone water, a means for suspending the food product, and one or a plurality of ultrasonic scrubbers that agitate the food product surface microcavities to allow for deeper penetration of the highly concentrated ozone water. It is the presence of the ultrasonic scrubbers that allow for access of the highly ozoneated water into contact with micro-organisms within the microcavities (due to disruption of the food surface) and that creates a better disinfection of food products using the inventive device.

Various food (meat) products were tested for disinfection using either a misting of ozonated water using prior art techniques, an immersion in either highly ozoneated water or standard immersion techniques, or contact with the inventive ozone fog. In each test the sample in contact with the ozone fog measured the lowest bacterial counts. The example below provides results from one of these tests.

EXAMPLE 1

This example provides the results of an experiment comparing various means for disinfecting food products using a standard ozone mist technique with large droplet sizes and lower concentrations of ozone and standard dipping techniques to the inventive fog. In this case the sample under test was a rump roast purchased from Safeway (a supermarket chain) and packaged 28 days earlier in Wichita, Kans.

Table 1 list results as measured by the Benton-Franklin health district. All analysis were performed using methods outlined in the districts *Standard Methods for the Examination of Water and Wastewater*, 18 edition.

TABLE 1

| $O_3$/ water ppm | application | Bacteria count | comment |
|---|---|---|---|
| 1.36 | Mist | $4.92 \times 10^5$ | Sample with least exposure to air |
| 4.25 | Fog | $1.3 \times 10^5$ | Least amount of applied water |
| 0.25 | Dip | $5.15 \times 10^5$ | Lowest conc. but full immersion |
| 5.1 | Mist | $1.28 \times 10^6$ | Sample on counter the longest before ozoneating (touched with hands |
| none | Control | $1.13 \times 10^6$ | Control sample no disinfection |

The ozone concentration in water was measured using an Ozotech calibrated 03 probe. It should be noted that the fog application yielded a bacterial count nearly 5 times lower than any other technique and nearly 10 time lower than the control sample. Table 1 also illustrates the inconsistency of a standard spray application independent of concentration. Finally, in accordance with the methods of analysis cited above the samples are measured at 24 hours from disinfection and again at 48 hours from disinfection. This "incubation" period allows "stressed" bacteria to fully recover. Standard techniques can at best stress bacteria located in microcavities, which is indicated by a low plate count followed by a much higher plate count after the set recovery time. The ozone fog application kills bacteria located in the micro-cavity that is indicated by a low plate count initially as well as after the recovery time.

EXAMPLE 2

This example provides the test results of another experiment of product samples of beef and chicken and determining bacterial counts (Benton County and Franklin County (Washington) Health Department) taken 24 hours after ozone exposure. The test compared the inventive ozone fog to control (no ozone exposure), a mist spray of ozone with large droplet size and a dip or immersion of ozone. The samples were not covered during the 24 hour waiting period and could have been recontaminated. The actual measurements was taken an additional 48 hours from the time of the swab to allow for proper incubation and this also could have allowed for stressed bacteria to recover. Table 2 provides the results showing a significantly greater effectiveness with the inventive fog despite less use of ozone and exposure.

TABLE 2

| Application | Diluted ozone conc. | % Bacteria 24 hrs later |
|---|---|---|
| None | na | 100% |
| fog | 0.04 | 12% |
| Spray/mist | 0.5 | 78% |
| dip | 0.25 | 46% |

These data further support the surprising results achieved with the inventive fog.

I claim:

1. A method for disinfecting irregular surfaces, comprising contacting a product having an irregular surface for disinfecting with a sterilizing ozone fog, wherein the ozone fog comprises water and ozone and wherein the fog is comprised of droplets having an average diameter of from about 0.0005 mm to about 0.05 mm, a weight of fog concentration in a treatment space of from about 0.08 g/m$^3$ to about 0.8 g/m$^3$, and an ozone concentration in water of from about 0.5 ppm to about 30 ppm.

2. The method for disinfecting irregular surfaces of claim 1 wherein the product having an irregular surface is a food product.

3. The method for disinfecting irregular surfaces of claim 2 wherein the food product is red meat or poultry.

4. A sterilizing agent-laden fog useful for disinfecting irregular surfaces wherein the fog comprises water and ozone as a sterilizing agent wherein the fog is comprised of droplets having an average diameter of from about 0.0005 mm to about 0.05 mm, a weight of fog concentration in a treatment space is of from about 0.08 g/m$^3$ to about 0.8 g/m$^3$.

5. The sterilizing agent-laden fog of claim 4 wherein the concentration of ozone in water of from about 0.5 ppm to about 30 ppm.

* * * * *